United States Patent [19]

Arai et al.

[11] Patent Number: 5,286,892
[45] Date of Patent: Feb. 15, 1994

[54] 2-TRIMETHOXYSILYLPROPIONATE

[75] Inventors: Masatoshi Arai; Takafumi Sakamoto; Yoshifumi Inoue; Kei Miyoshi, all of Annaka, Japan

[73] Assignee: Shin-Etsu Chemical Co., Ltd., Tokyo, Japan

[21] Appl. No.: 985,868

[22] Filed: Dec. 4, 1992

[30] Foreign Application Priority Data

Dec. 4, 1991 [JP] Japan .................. 3-348138

[51] Int. Cl.$^5$ .............. C07F 7/08; C07F 7/18
[52] U.S. Cl. .................. 556/438
[58] Field of Search ................... 556/438

[56] References Cited

U.S. PATENT DOCUMENTS

| | | | |
|---|---|---|---|
| 2,589,447 | 3/1952 | Sommer | 556/438 |
| 2,723,987 | 11/1955 | Speier | 556/438 X |
| 2,802,852 | 8/1957 | George | 556/438 X |
| 3,109,011 | 10/1963 | Pike et al. | 556/438 |
| 3,657,147 | 4/1972 | Pohl et al. | 556/438 X |
| 5,124,469 | 6/1992 | Takago et al. | 556/438 |

FOREIGN PATENT DOCUMENTS 2904220 8/1980 Fed. Rep. of Germany .
3602490 8/1987 Fed. Rep. of Germany .

OTHER PUBLICATIONS

Journal of the Chemical Society, Chemical Communications, No. 18, Sep. 15, 1991, pp. 1247–1248, R. Takeuchi, et al., "Highly Regioselective Carbonylation of Vinylsilanes: A Remarkable Effect of Organosilicon Substituent".

Primary Examiner—Paul F. Shaver
Attorney, Agent, or Firm—Oblon, Spivak, McClelland, Maier & Neustadt

[57] ABSTRACT

The present novel organosilicon compound is a 2-trimethoxysilylpropionate represented by the following formula

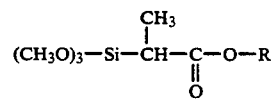

wherein R represents a monovalent hydrocarbon group having 6 to 12 carbon atoms. This ester reacts efficiently with alcohols and silanols and is useful, for example, as a terminal alkoxysilylating agent for organopolysiloxanes such as industrially useful $\alpha,\omega$-dihydroxypolydimethylsiloxane, or as a surface treatment for silicas, or as a storage stabilizer that serves as a scavenger of an alcohol for alcohol elimination type RTV. Further, since the present organosilicon compound is a three-functional alkoxysilane having three methoxy groups in the molecule, it is useful as a curing agent for alcohol elimination type RTV.

1 Claim, 2 Drawing Sheets

2-TRIMETHOXYSILYLPROPIONATE

BACKGROUND OF THE INVENTION

1. Field of the Invention

The present invention relates to a novel organosilicon compound, and more particularly to a novel organosilicon compound useful, for example, as an alkoxysilylating agent, a surface treatment, a curing agent, or a storage stabilizer such as an alcohol scavenger.

2. Description of the Prior Art

As an agent for alkoxysilylating the terminals of an organopolysiloxane such as $\alpha,\omega$-dihydroxypolydimethylsiloxane, various alkoxysilanes are known. However, the conventionally known alkoxysilylating agents are not still satisfactory, for example, in reactivity, and alkoxysilylating agents further improved in properties such as reactivity are desired.

SUMMARY OF THE INVENTION

Therefore, an object of the present invention is to provide a novel organosilicon compound particularly useful as a terminal alkoxysilylating agent for organopolysiloxanes.

According to the present invention, there is provided a 2-trimethoxysilylpropionate represented by the following general formula (1):

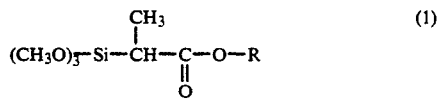

wherein R represents a monovalent hydrocarbon group having 6 to 12 carbon atoms.

In the above general formula (1), the monovalent hydrocarbon group R having 6 to 12 carbon atoms may be straight-chain, cyclic, or branched, and examples include a straight-chain alkyl group such as hexyl, heptyl, octyl, nonyl, and decyl, a cyclic alkyl group such as cyclohexyl, and a branched alkyl group such as 2-ethylhexyl. The most preferable R in the present invention is 2-ethylhexyl.

DETAILED DESCRIPTION OF THE INVENTION

Figure 1:
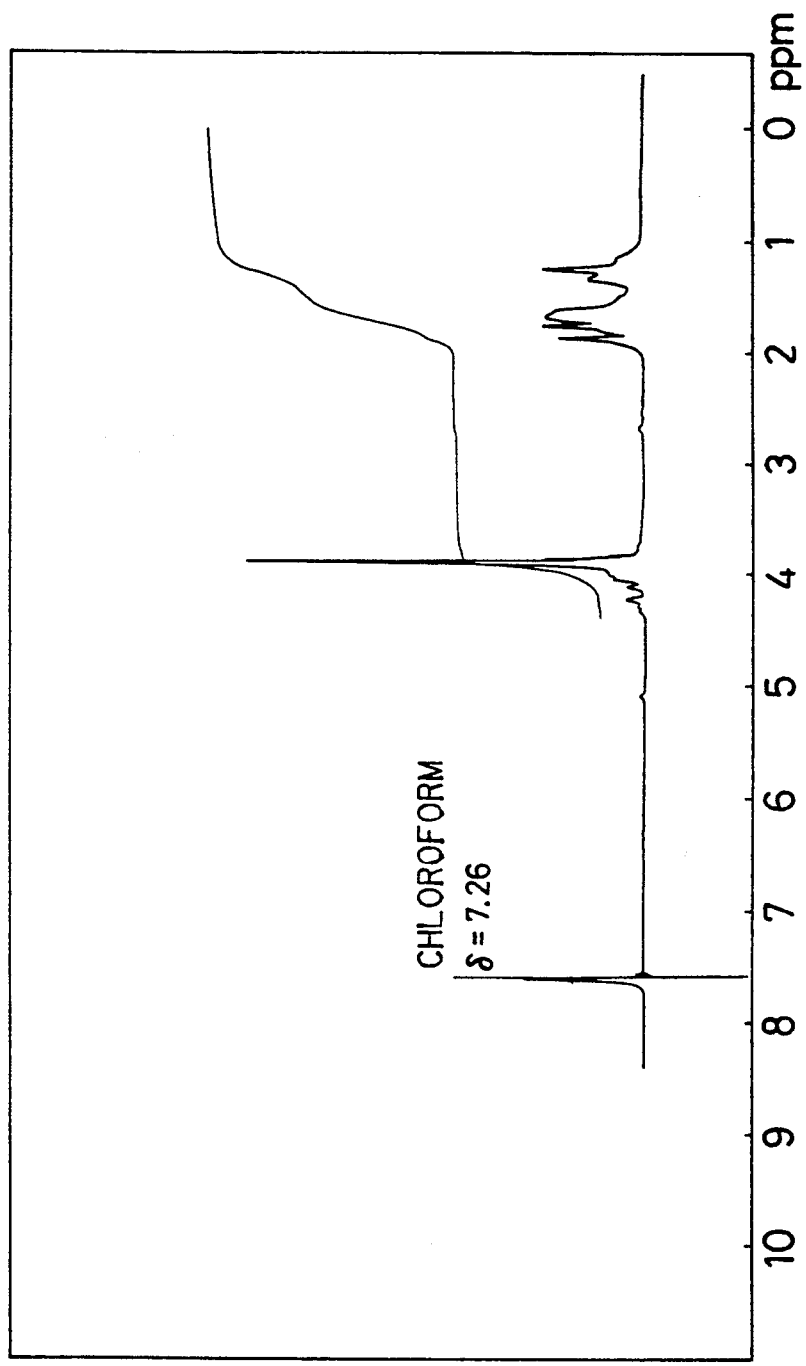
FIG. 1 shows the NMR chart of the reaction product obtained in Example 1.

The present organosilicon compound represented by the general formula (1) reacts efficiently with alcohols and silanols because its silicon-carbon bond has an $\alpha$-silyl ester structure which splits under relatively mild conditions. Therefore, this novel organosilicon compound is useful, for example, as a terminal alkoxysilylating agent for organopolysiloxanes such as industrially useful $\alpha,\omega$-dihydroxypolydimethylsiloxane, or as a surface treatment for silicas, or as a storage stabilizer that serves as a scavenger, for example, of an alcohol for alcohol elimination-type RTV. Further, since the present organosilicon compound is a three-functional alkoxysilane having three methoxy groups in the molecule, it is useful as a curing agent for alcohol elimination type RTV.

Process of the Preparation

The present 2-trimethoxysilylpropionate can be produced by reacting an acrylate with trimethoxysilane. The reaction can be represented, for example, by the following formula (2):

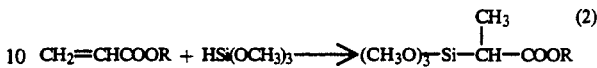

wherein R has the same meaning as defined above.

As apparent from the above formula (2), this reaction is an addition reaction of a hydrosilyl group (SiH) to a carbon-carbon double bond (C=C), and generally this reaction is carried out in the presence of an addition reaction catalyst. That catalyst includes a platinum family metal catalyst such as a platinum catalyst, a palladium catalyst, and a rhodium catalyst, with particular preference given to a platinum catalyst. Examples of the platinum catalyst include platinum black, solid platinum supported on a carrier such as alumina and silica, chloroplatinic acid, a complex of chloroplatinic acid with an olefin, and a complex of chloroplatinic acid with a vinylsiloxane. The amount of these catalysts to be used is a so called catalytic amount, and, for example, the catalyst is used in an amount of 0.1 to 1,000 ppm in terms of the platina family metal based on the total amount of the acrylate and the trimethoxysilane.

This reaction is generally carried out desirably at a temperature of 60° to 120° C. and can be carried out without any solvent but if necessary the reaction can be carried out with the use of a suitable solvent so long as the solvent does not affect adversely, for example, the addition reaction.

In the reaction of the above formula (2), in addition to the present organosilicon compound, small amounts of isomers represented by the following formulas (3) and (4):

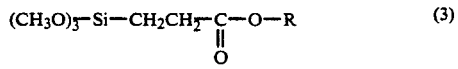

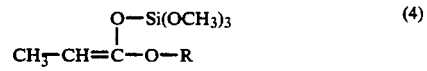

wherein R has the same meaning as defined above are produced as by-products.

Although these by-products can be removed by means of purification such as distillation, their amounts are very small and since they are isomers of the present organosilicon compound and do not affect adversely the properties of the present organosilicon compound, the reaction product in the formula (2) can be used, for example, as a terminal alkoxysilylating agent, a surface treatment for silicas, a storage stabilizer, and a curing agent as it is.

Example 1

921.4 g (5 mol) of 2-ethylhexyl acrylate, 0.46 g of chloroplatinic acid ($H_2PtCl_6 \cdot 6H_2O$), 0.92 g of Irganox 1330 (a polymerization inhibitor manufactured by Ciba-Geigy), and 0.92 g of 2,6-di-t-butyl-4-methylphenol (a polymerization inhibitor manufactured by Ciba-Geigy) were placed in a 3-litter four-necked flask equipped with a stirrer, a reflux condenser, a thermometer, and a dropping funnel, and the resulting mixture was heated to a temperature of 80° C. with stirring.

When 672.1 g (5.5 mol) of trimethoxysilane was added dropwise to the mixture with stirring, it was recognized that heat was generated and the reaction temperature reached 80° to 90° C., at which the reaction system was kept for 3 hours.

After the completion of the reaction, the reaction mixture was subjected to vacuum distillation to obtain 968 g (yield: 63%) of a fraction having a boiling point of 146° to 148° C./5 mmHg.

According to the gas chromatographic analysis thereof, the fraction contained three components, and from the results of the analysis given below it was found that the following compounds (a), (b), and (c) were contained in a weight ratio of a : b : c of 91 : 2 : 7.

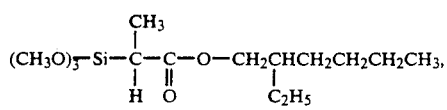
(a)

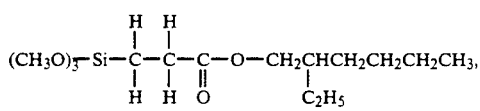
(b)

-continued
and

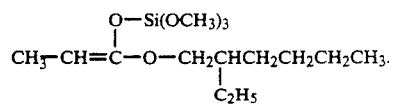
(c)

Figure 2:
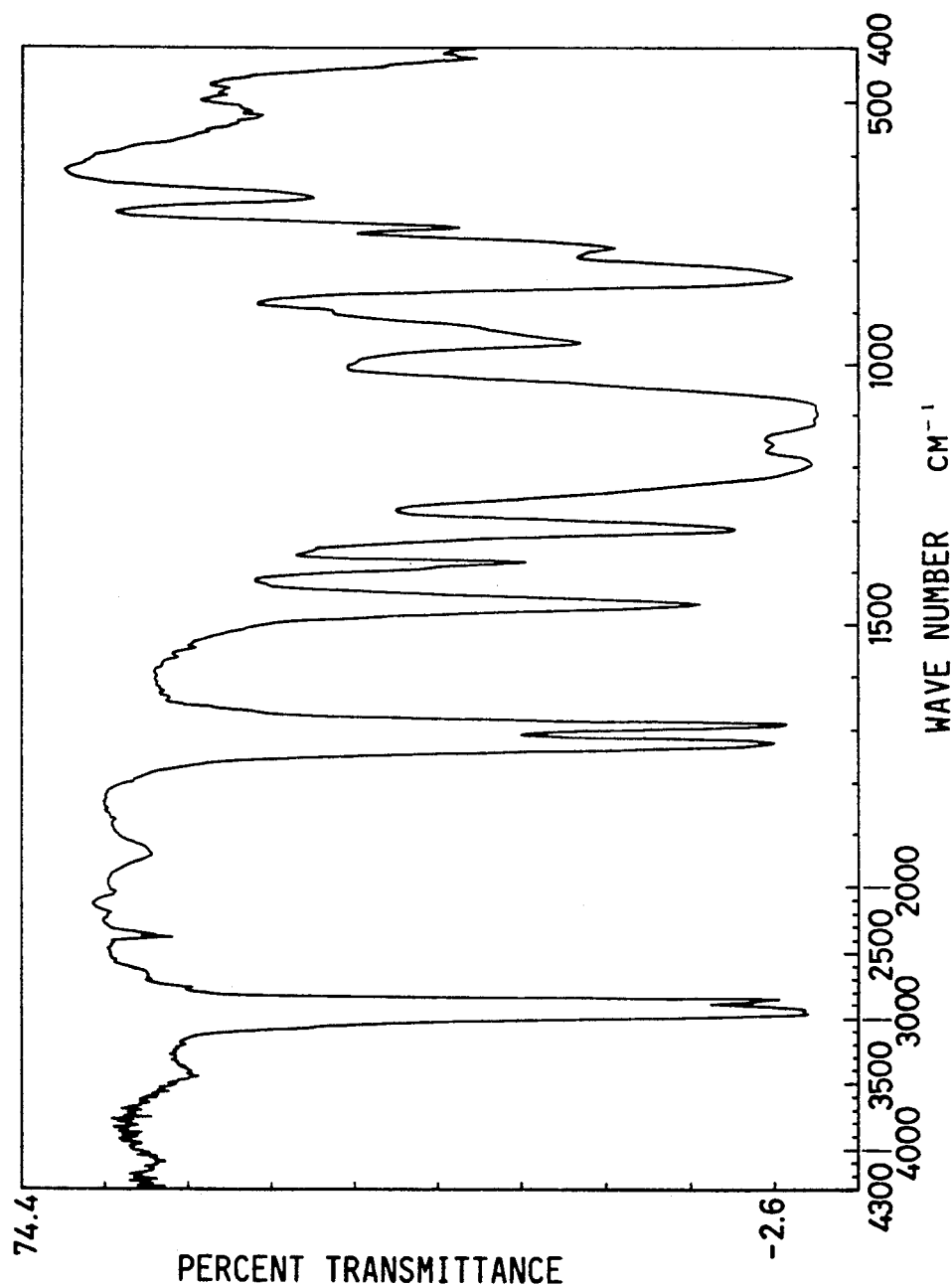
FIG. 2 shows the IR chart of that reaction product.

GC-MS analysis
m/e: 306 (molecular weight: 306)
NMR analysis: The chart is shown in FIG. 1.
δ (ppm)
3.79 (q, 1H, Si—CH)
3.76 (q, 2H, —O—CH$_2$)
3.60 (s, 9H, Si—O—CH$_3$)
1.66 to 0.66 (broad, 18H, CH, CH$_2$, CH$_3$)
IR analysis
The chart is shown in FIG. 2.

We claim:
1. A 2-trimethoxysilylpropionate represented by the following formula (1):

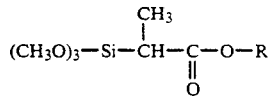
(1)

wherein R represents the 2-ethylhexyl group.

* * * * *